US008152909B2

(12) United States Patent
Kellogg (10) Patent No.: US 8,152,909 B2
(45) Date of Patent: Apr. 10, 2012

(54) GAS CHROMATOGRAPHY CHECK VALVE AND SYSTEM

(75) Inventor: Christopher Cameron Kellogg, Walnut Creek, CA (US)

(73) Assignee: Bruker Chemical Analysis B.V., Goes (NL)

( * ) Notice: Subject to any disclaimer, the term of this patent is extended or adjusted under 35 U.S.C. 154(b) by 439 days.

(21) Appl. No.: 12/416,745

(22) Filed: Apr. 1, 2009

(65) Prior Publication Data

US 2010/0251896 A1 Oct. 7, 2010

(51) Int. Cl.
*B01D 53/02* (2006.01)
*F16K 15/02* (2006.01)

(52) U.S. Cl. ............. 96/101; 96/105; 96/106; 73/23.42; 137/540; 137/542; 137/543.15

(58) Field of Classification Search .............. 96/101, 96/105, 106; 73/23.35, 23.41, 23.42; 137/511, 137/535, 540, 542, 543.15
See application file for complete search history.

(56) References Cited

U.S. PATENT DOCUMENTS

| 1,767,538 | A | * | 6/1930 | Mahan | 137/515.3 |
|---|---|---|---|---|---|
| 3,097,660 | A | | 7/1963 | Priesmeyer | |
| 3,225,520 | A | | 12/1965 | Burow | |
| 3,749,122 | A | * | 7/1973 | Gold | 137/515.7 |
| 3,756,273 | A | | 9/1973 | Hengesbach | |
| 3,945,396 | A | | 3/1976 | Hengesbach | |

(Continued)

FOREIGN PATENT DOCUMENTS

GB 1219389 A 4/1968

(Continued)

OTHER PUBLICATIONS

Kaufmann A., Prevention of Vapor Overflow in Splitless Injection by a Novel Injector Design, Journal of High Resolution Chromatography, V.21 1998.

*Primary Examiner* — Robert Clemente
(74) *Attorney, Agent, or Firm* — Law Offices of Paul E. Kudirka (57) ABSTRACT

An apparatus, system, and method are disclosed for a gas chromatography (GC) system with a check valve. The check valve is situated downstream from the electronic flow control module and upstream of the injector. When a sample is volatized in the injector, the check valve closes into a checked position and prevents solvent and sample from backing into the gas delivery line. In certain embodiments, the check valve has a conical plug that fits into a seat that has an aperture. When the conical plug is depressed, the conical plug engages the sides of the aperture and seals the check valve, preventing solvent and sample from backing through the check valve. In certain embodiments, the change in pressure caused by over-pressurization in the injector, combined with the force applied by a spring on the conical plug, depresses the plug such that it seals the aperture.

12 Claims, 5 Drawing Sheets

U.S. PATENT DOCUMENTS

| | | | |
|---|---|---|---|
| 4,002,070 A | 1/1977 | Howell | |
| 4,662,831 A | 5/1987 | Bennett | |
| 4,791,950 A | 12/1988 | Pedersen | |
| 4,962,042 A | 10/1990 | Morabito | |
| 4,984,306 A | 1/1991 | Sumerix | |
| 5,123,276 A | 6/1992 | Hartman | |
| 5,245,976 A * | 9/1993 | Faull | 123/587 |
| 5,338,514 A | 8/1994 | Morabito | |
| 5,415,303 A * | 5/1995 | Hodges et al. | 213/43 |
| 5,827,945 A | 10/1998 | Arnold | |
| 5,872,306 A | 2/1999 | Arnold | |
| 5,927,323 A * | 7/1999 | Kikuchi et al. | 137/514.5 |
| 6,223,584 B1 * | 5/2001 | Mustacich et al. | 73/23.41 |
| 6,513,546 B2 * | 2/2003 | Katsura | 137/540 |
| 6,627,454 B2 | 9/2003 | Amirav et al. | |
| 6,905,318 B2 * | 6/2005 | Kouno et al. | 417/559 |
| 7,144,502 B2 * | 12/2006 | Fermier et al. | 210/198.2 |
| 7,832,422 B2 * | 11/2010 | Endoh et al. | 137/540 |

FOREIGN PATENT DOCUMENTS

| | | |
|---|---|---|
| GB | 1111443 A | 1/1971 |
| KR | 20-0213462 Y1 | 2/2001 |
| KR | 10-2007-0106858 A | 11/2007 |

\* cited by examiner

GAS CHROMATOGRAPHY CHECK VALVE AND SYSTEM

FIELD OF THE INVENTION

This invention relates to gas chromatography (GC) and gas chromatography hybrid instruments. More particularly, this invention relates to the use of check valves in GC instruments to improve operation.

BACKGROUND OF THE INVENTION

Gas chromatography is a popular analytical technique used to separate and analyze the composition of samples. Gas chromatography encompasses a range of different variations, such as gas-solid chromatography (GSC) and gas-liquid chromatography (GLC), and includes hyphenated methods such as gas chromatography-mass spectrometry (GC/MS). As more precision and detail is demanded from GC systems, the need for increased sensitivity in these systems grows.

As a result, problems such as tailing and carryover become more important. Tailing refers to asymmetry of a peak such that the front is steeper than the rear. Carryover refers to the problem of having sample from a previous analysis, or earlier in the same analysis, showing up later in time or otherwise saturating detectors with unwanted solvent molecules. Where greater sensitivity is required, tailing and carryover problems that can often be ignored suddenly become important.

SUMMARY OF THE INVENTION

As is evident from the foregoing discussion, a need exists for a GC system that is less susceptible to tailing and carryover problems. Such a GC system and a check valve apparatus are disclosed herein.

The GC system includes an electronic flow control module that provides a carrier gas that elutes a sample through a column, an injector that receives a sample to be analyzed, and a vaporizer that vaporizes the sample introduced into the injector. A gas delivery line connects the electronic flow control module and the injector, allowing flow of carrier gas from the electronic flow control module to the injector. The GC system also includes a column having a stationary phase. The column connects to the injector, and the carrier gas and vaporized sample pass through the column where the output of the column is analyzed by a detector.

The GC system also includes a check valve situated in the gas delivery line downstream of the electronic flow control module and upstream of the injector. The check valve seals when there is a change in pressure in the injector that reverses the flow in the gas chromatography system. The check valve substantially prevents back flow of sample into the gas delivery line.

In certain embodiments, the check valve has a valve body with a channel, a gas delivery line outlet that connects the channel to the injector by way of the gas delivery line, and a gas delivery line inlet that connects the channel to the electronic flow control module. The check valve may also include a seat situated within the channel between the gas delivery line outlet and the gas delivery line inlet. The seat has an aperture that continues the channel, thus allowing gas to flow through the channel when the aperture is not sealed. In such an embodiment, the check valve also includes a conical plug that engages the sides of the aperture and thus closes the channel in response to over-pressurization in the injector during sample volatilization.

The conical plug may also include a lip at its base that engages the top of the seat when the conical plug is depressed. In certain embodiments, the check valve also includes a stabilizer that has apertures in it that continue the channel. The stabilizer maintains the position of the conical plug in relation to the seat.

A spring may be situated between the stabilizer and the conical plug in order to provide a force that causes the conical plug to engage the sides of the aperture of the seat. In such an embodiment, the conical plug engages the aperture when the force exerted on the conical plug by the gas entering the channel through the gas delivery inlet is less than the force exerted on the conical plug by a gas entering the channel through the gas delivery outlet in combination with the closing force exerted on the conical plug by the spring.

The check valve may also include spacers that position the seat, the conical plug, and the stabilizer within the channel and that also reduce the empty volume of the channel. The check valve may also include a filter that filters contaminant that backs into the check valve through the gas delivery outlet.

Reference throughout this specification to features, advantages, or similar language does not imply that all of the features and advantages that may be realized with the present invention should be or are in any single embodiment of the invention. Rather, language referring to the features and advantages is understood to mean that a specific feature, advantage, or characteristic described in connection with an embodiment is included in at least one embodiment of the present invention. Thus, discussion of the features and advantages, and similar language, throughout this specification may, but do not necessarily, refer to the same embodiment.

Furthermore, the features, advantages, and characteristics of the apparatus, system, and method described herein may be combined in any suitable manner in one or more embodiments. One skilled in the relevant art will recognize that the invention may be practiced without one or more of the specific features or advantages of a particular embodiment. In other instances, additional features and advantages may be recognized in certain embodiments that may not be present in all embodiments of the invention.

These features and advantages of the present invention will become more fully apparent from the following description and appended claims, or may be learned by the practice of the invention as set forth hereinafter.

BRIEF DESCRIPTION OF THE DRAWINGS

In order that the advantages of the invention will be readily understood, a more particular description of the invention briefly described above will be rendered by reference to specific embodiments that are illustrated in the appended drawings. Understanding that these drawings depict only certain illustrative embodiments and are not therefore to be considered to be limiting of its scope, further embodiments of the invention will be described and explained with additional specificity and detail through the use of the specification, claims, and accompanying drawings, in which:

DETAILED DESCRIPTION OF THE INVENTION

Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment. Furthermore, the described features, structures, or characteristics of the invention may be combined in any suitable manner in one or more embodiments. Additionally, one skilled in the relevant art will recognize that the invention may be practiced without one or more of the specific details described herein, or with other methods, components, materials, and so forth. In other instances, well-known structures, materials, or operations are not shown or described in detail to avoid obscuring aspects of the invention.

Figure 1:
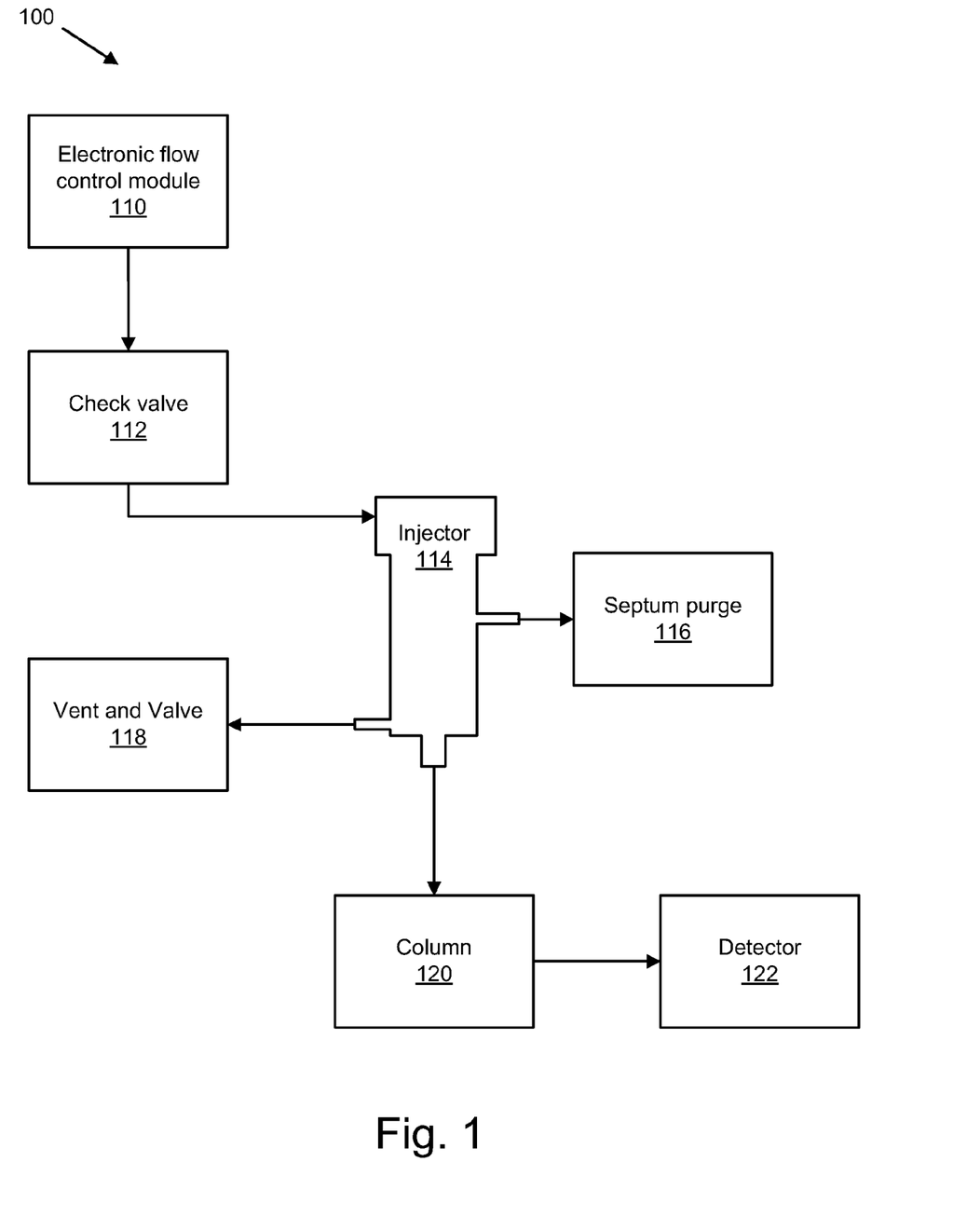
FIG. 1 is an illustrative block diagram of one embodiment of a gas chromatography system.

FIG. 1 shows a basic illustration of a GC system 100 that includes an electronic flow control module 110, a check valve 112, an injector 114, a septum purge 116, a vent and valve 118, a column 120, and a detector 122. The GC system 100 may include additional components not shown in FIG. 1. Those of skill in the art will appreciate the various additional components and modifications that may be utilized in the GC system 100.

The flow control module 110 provides the mobile phase for the GC system. The mobile phase is a carrier gas which elutes the sample through the column 120. Popular carrier gases include nitrogen, helium, and hydrogen. The flow control module 110 may include flow controllers to regulate the flow of the carrier gas. For example, the flow control module 110 may include a pressure controller and a flow controller. In certain embodiments, the flow control module 110 may be an electronic flow control module. The flow control module 110 may be a mechanical flow control module. The flow control module 110 may also use manual pneumatics. In certain embodiments the flow control module 110 may simply be a connection to a gas supply such as a gas tank or a generator. The flow control module 110 supplies the carrier gas through a gas delivery line that connects the flow control module and the injector 114.

The injector 114 is used to introduce the sample to be tested into the column 120 in an accurate manner. The sample is introduced into the injector and combined with carrier gas to move the sample through the column 120. In one embodiment, the sample is a liquid when it is introduced into the injector 114. A vaporizer vaporizes the liquid sample, and the carrier gas and vaporized sample are introduced to the column 120. The vaporizer may be part of the injector 114 or, in certain embodiments, may be separate from the injector 114. In certain embodiments, the sample is flash vaporized in a heated liner of the injector 114.

The injector 114 may also be a split/splitless injector 114. In such an embodiment, the CG system 100 includes a vent and valve 118. The user can adjust the split ratio to control the amount of sample that enters the column 120 relative to the amount of sample that exits the injector 114 through the vent and valve 118. The vent and valve 118 may be closed completely to facilitate splitless injection. Splitless injection, with the vent and valve 118 closed, may be preferable for trace analysis or where improved sensitivity is required.

A septum purge 116 uses a gas to sweep out residue from the injector 114 through a purge vent. The septum purge 116 may, for example, use the carrier gas to purge the septum, thus reducing the likelihood that material will remain in the injector 114 and contaminate the GC system 100.

The column 120 includes the stationary phase, and is connected to the injector 114. As the carrier gas elutes the vaporized sample through the column 120, the sample is separated into constituent components. In certain embodiments, the column 120 may be a capillary column or a packed column. As the column temperature influences separation, the column 120 typically has an associated column oven used to control the column temperature as needed.

The detector 122 provides a response signal that represents the output of the column 120. For example, the detector may convert the sample analytes leaving the column 120 into an electrical signal whose strength depends on the amount or concentration of the analytes. For example, a flame ionization detector (FID), electron capture detector (ECD), or mass spectrometer may be used as the detector 122.

When a sample is volatized in the injector 114, the injector 114 may undergo a period of over pressurization due to the restricted flow within the GC system 100. This change in pressure in the injector 114 can temporarily reverse the normal flow within the GC system 100. The change in pressure may thus push sample (whether in solvent or gaseous form) into the gas delivery line and, in extreme cases, even into the electronic flow control module 110 itself. The problem is particularly challenging when the column outlet is at or near a vacuum, such as in GC/MS and other GC hyphenated systems. In addition, the sudden change in pressure in the injector 114 during sample volatilization may cause the electronic flow control module 110 to reduce the carrier gas delivery pressure, which exacerbates the reversal of flow. Over pressurization is also more likely when the vent and valve 118 of the injector 114 is closed or significantly restricted, which further restricts the flow within the GC system 100.

The check valve 112 is situated in the gas delivery line downstream from the electronic flow control module 110 and upstream from the injector 114. The check valve 112 is a valve that permits gas to flow in one direction only; that is, the check valve 112 is situated to permit gas to flow only from the electronic flow control module 110 towards the injector 114. The check valve 112 seals and stops gas and liquids from flowing towards the electronic flow control module 110. Check valves such as check valve 112, however, are not perfect—there may be some reversal of flow before the seal is made, and the seal may not be perfect. However, the check valve 112 substantially prevents back flow of sample into the gas delivery line.

In one embodiment, the check valve 112 is situated close to the injector 114 to reduce the volume between the check valve 112 and the injector 114 in order to minimize back flow. The check valve 112 seals when there is a change in pressure in the injector 114 that reverses flow in the gas chromatography system. This seal prevents solvent from moving through the gas delivery line beyond the check valve 112 and causing contamination in the gas delivery line. Instead, the check valve 112 forces solvent and sample through the injector 114.

When the carrier gas is flowing normally from the electronic flow control module 110, and in the absence of any events that alter the pressure in the GC system 100, the pressure caused by the carrier gas flowing out of the electronic flow control module 110 provides sufficient force to open the check valve 112 and allow the carrier gas to pass through it and to the injector 114. A check valve 112 with an appropriate cracking pressure may thus be selected based on the configuration of the electronic flow control module 110. In one embodiment, the check valve 112 may be a diaphragm check valve, a swing check valve, a disc check valve, or other appropriate check valve type that provides a seal during volatilization in the injector 114.

In certain embodiments, check valves 112 may also be placed in the line connecting the septum purge 116 to the injector 114 and in the line connecting the vent and valve 118 to the injector 114. One or more additional check valves 112 thus positioned in the gas chromatography system 100 may also help improve the quality and sensitivity of the gas chromatographer.

Figure 2:
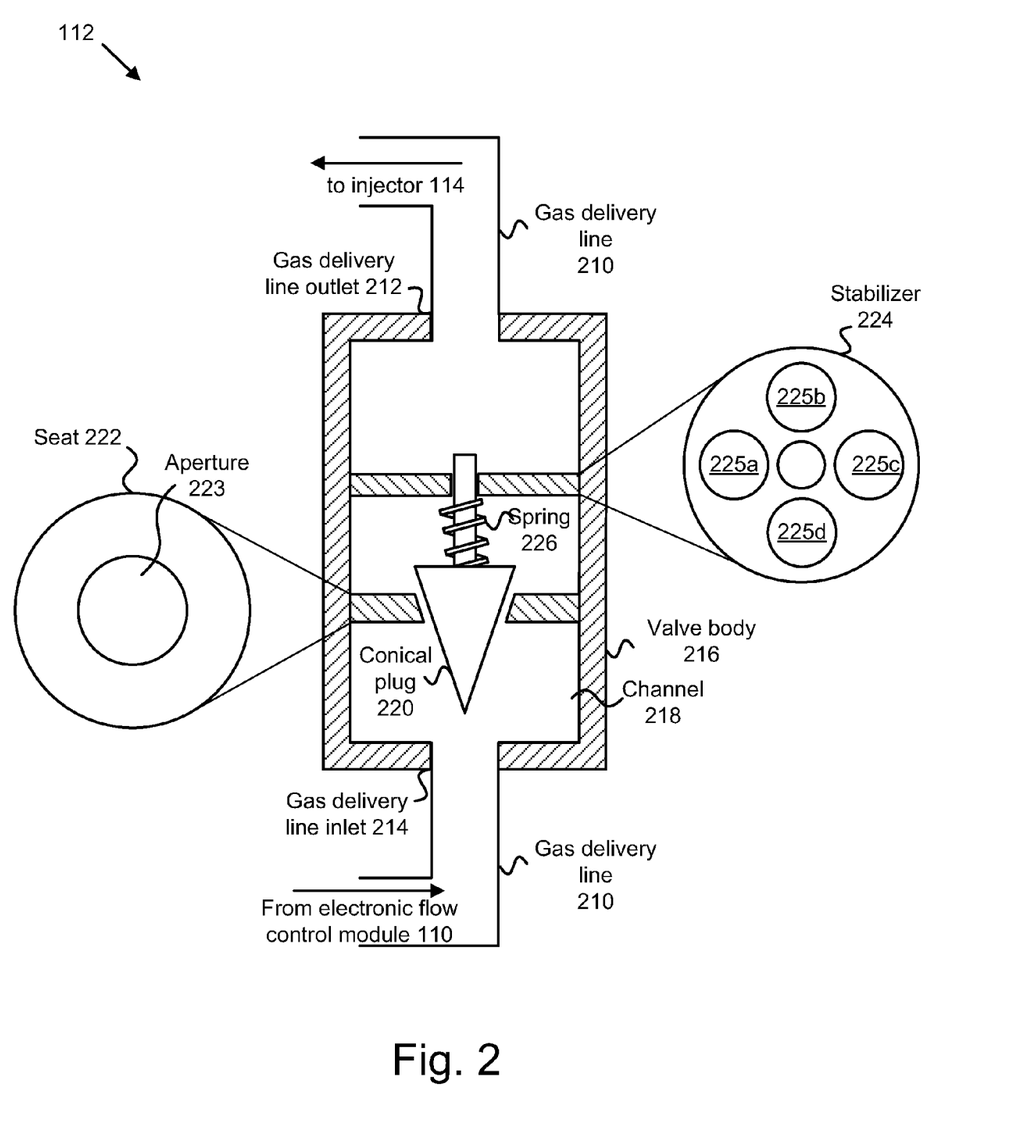
FIG. 2 is a view of a check valve for use in a gas chromatography system.

FIG. 2 shows one embodiment of a check valve 112 that prevents back flow in a gas chromatography system. The embodiments of the check valve 112 shown below are not to scale. The check valve 112 has a valve body 216 with a channel 218. The valve body 216 may be plastic or any other suitable material. The channel 218 allows carrier gas to flow into the check valve 112 from the electronic flow control module 110, through the check valve 112, and out of the check valve 112 to the injector 114.

A gas delivery line inlet 214 allows carrier gas from the electronic flow control module 110 to enter the channel 218. The gas delivery line inlet 214 connects to the gas delivery line 210. This connection connects the check valve 112 to the electronic flow control module 110. The gas delivery line outlet 212 allows carrier gas from the electronic flow control module 110 to exit the channel 218. The gas delivery line outlet 212 interfaces with the gas delivery line 210 and connects to the check valve 112 to the injector 114.

In one embodiment, the check valve 112 also includes a seat 222 that is situated within the channel 218 and between the gas delivery line outlet 212 and the gas delivery line inlet 214. As shown in FIG. 2, the seat 222 also includes an aperture 223. The aperture 223 continues the channel 218 such that the carrier gas may flow through the aperture 223 when the check valve 112 is in a flowing position. FIG. 2 shows the check valve 112 in a flowing position. In one embodiment, the aperture 223 is circular. The aperture 223 may have angled walls with an angle that is equal to the exterior angle of the conical plug 220 described below. In such an embodiment, the conical plug 220 may provide a better seal to block flow when it is depressed and engages the sides of the aperture 223.

Figure 3:
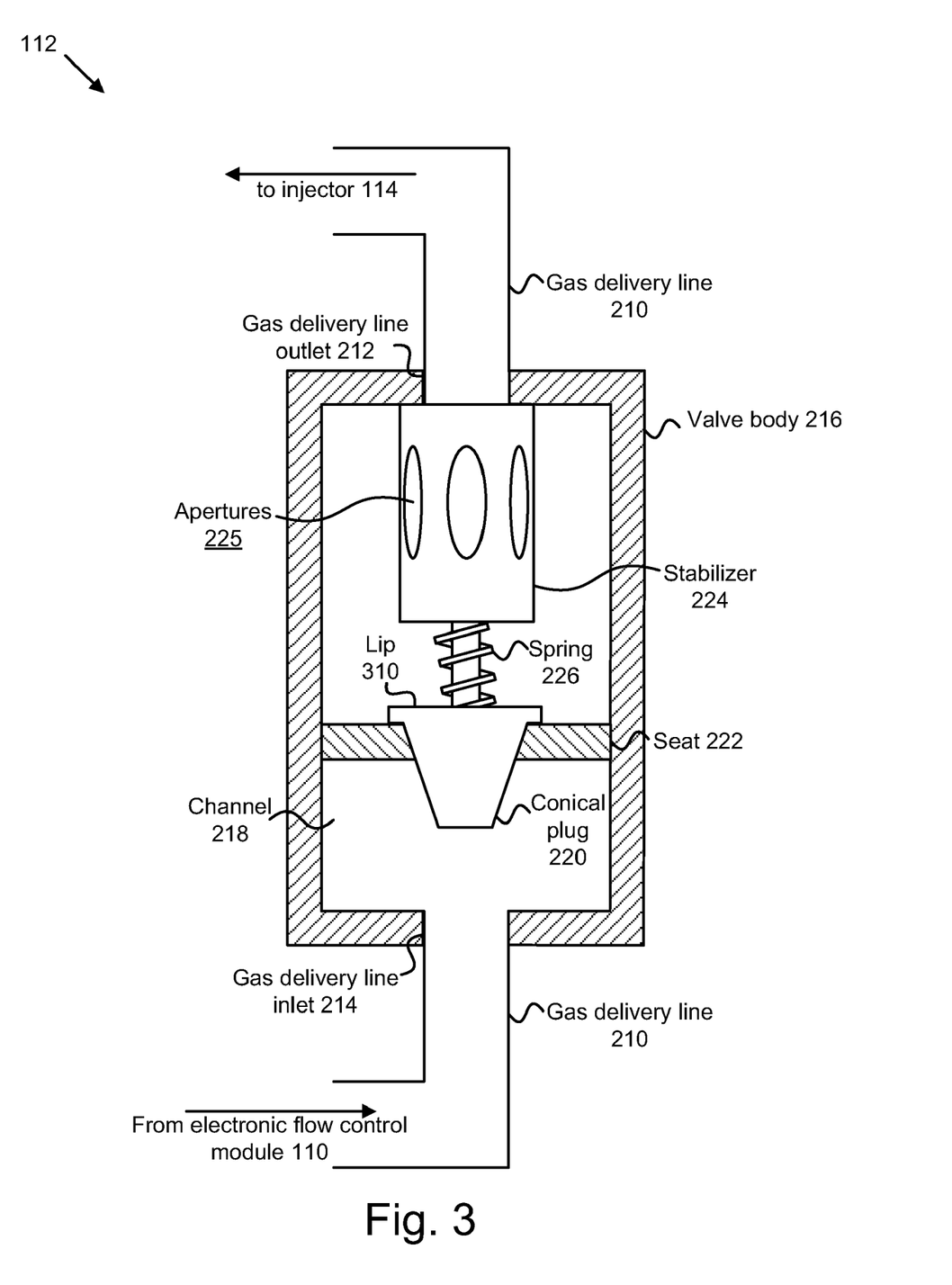
FIG. 3 is a view of another embodiment of a check valve for use in a gas chromatography system.

In one embodiment, the check valve 112 also includes a conical plug 220 that engages the sides of the aperture 223 and thus seals the channel 218 when the conical plug 220 is sufficiently depressed. In one embodiment, as shown in FIG. 2, the apex of the conical plug 220 is directed towards the gas delivery line inlet 214. The conical plug 220 may have a shape other than a true cone. For example, the conical plug 220 may have a rounded apex, or have a blocked apex, as shown in FIG. 3. The conical plug 220 may have the shape of a conical polyhedron. In one embodiment, the conical plug 220 engages the sides of the aperture 223 and closes the channel 218 in response to over-pressurization in the injector 114 during sample volatilization.

The check valve 112 may also include a stabilizer 224 that is situated within the channel 218 between the gas delivery outlet 212 and the seat 222. The stabilizer 224 may also include one or more apertures 225a-d that continue the channel 218 and thus allow carrier gas to pass through them. The stabilizer 224 maintains the position of the conical plug 220 relative to the seat 222. For example, the stabilizer 224 may keep the conical plug 220 properly position with respect to the seat 222 and the aperture 223.

The check valve 112 may also include a spring 226. In certain embodiments, the spring 226 is situated between the stabilizer 224 and the conical plug 220 and the force of the spring on the conical plug 220, directed towards the aperture 223, depresses the conical plug 220 to engage the sides of the aperture 223 of the seat 222. In such embodiments, the natural position for the check valve 112 is the checked position where the conical plug 220 seals the aperture 223. The pressure of the carrier gas that enters through the gas delivery line inlet 214 on the conical plug 220 opens the check valve 112 to the flowing position.

In one embodiment, the conical plug 220 engages the walls of the aperture 223 when the opening force exerted on the conical plug 220 by the carrier gas entering at the gas delivery line inlet 214 is less than the opposing force exerted on the base of the conical plug 220 by the spring 226 in combination with the force exerted on the conical plug 220 by a gas entering the channel 218 through the gas delivery line outlet 212. When the pressure at the gas delivery inlet 214 is greater, the conical plug 220 is pushed open and the carrier gas flows through the aperture 223.

The check valve 112 thus reduces the amount of solvent and sample that may be pushed back into the gas delivery line 210 during volatilization. For example, when a liquid sample is volatized in the injector 114, the liquid may expand to several thousand times its volume as it becomes a gas. Where the volatilization occurs quickly, the flow in the GC system may be reversed, with liquid sample and gaseous sample being pushed up through the gas delivery line and towards the electronic flow control module 110. The check valve 112 shuts in response to the change in flow and prevents the sample from being pushed backwards. As a result, tailing and carryover problems are significantly reduced. The check valve 112 may also include a filter to filter any stray contaminant that backs into the check valve 112 through the gas delivery line outlet 212.

FIG. 3 shows a second embodiment of a check valve 112. In FIG. 3, the check valve 112 is in the checked position and thus substantially seals the check valve 112. FIG. 3 also shows a second configuration for a stabilizer 224 situated within the channel 218 and between the gas delivery line outlet 212 and the seat 222. The stabilizer 224 maintains the position of the conical plug 220 in relation to the seat 222.

FIG. 3 also shows the conical plug 220 with a lip 310. In certain embodiments, the conical plug 220 has a lip 310 that engages the top of the seat 222 when the conical plug 220 is depressed and seals the aperture 233. The lip 310 may provide a better seal of the aperture 233 and increase the sealing surface area. FIG. 3 also shows a second embodiment of the conical plug 220 with a flattened apex.

Figure 4:
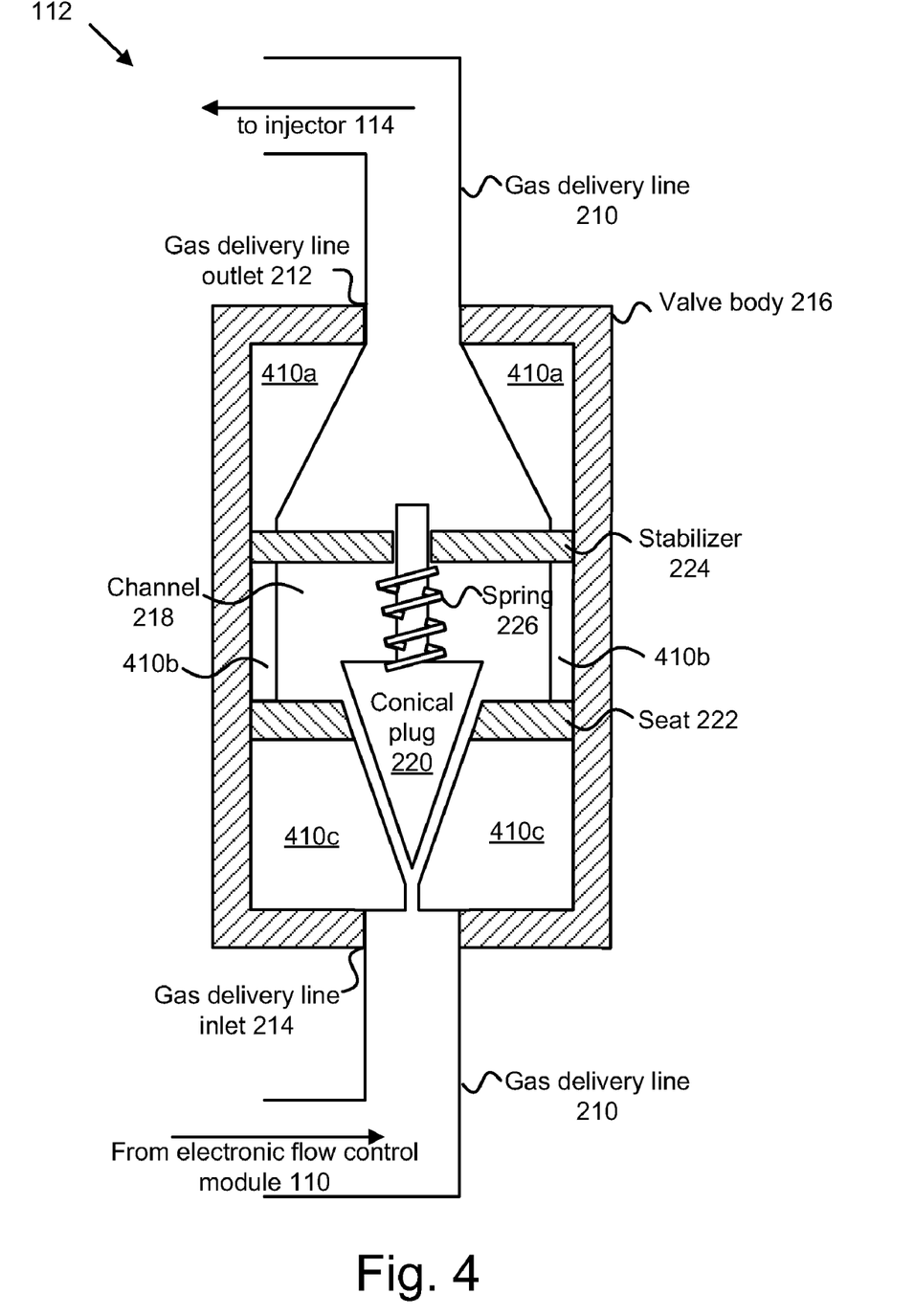
FIG. 4 is a view of another embodiment of a check valve for use in a gas chromatography system.

FIG. 4 illustrates an additional embodiment of a check valve 112. FIG. 4 shows the check valve 112 of FIG. 2, with the addition of spacers 410a-c. In certain embodiments, the check valve 112 includes spacers 410a-c that situate the various components of the check valve 112, such as the seat 222 and the stabilizer 224. The spacers 410a-c may also be designed to reduce the empty volume of the channel 218 while allowing the carrier gas to pass through the check valve 112 when it is in the flowing position.

The spacers 410a-c may be inserts that are separate from the valve body 216. In certain embodiments, the spacers 410a-c may be part of the valve body 216. The stabilizer 224 and the seat 222 may similarly be part of the valve body 216 in certain embodiments.

While the embodiments shown in FIGS. 2 though 4 have shown a spring 226 providing a closing force on the conical plug 220, other embodiments of the check valve 112 may use different approaches for providing a closing force. For example, one embodiment may utilize a compliant material to provide a restoring force that moves the check valve 112 into the checked position. Other embodiments may use electronic or magnetic devices to provide such a force. In certain embodiments, the flowing position may be the normal position for the check valve 114. In certain embodiments, the check valve 112 may not have a normal position. In other embodiments, the check valve 112 may use lever action instead of linear travel for the check valve 112 actuation.

Figure 5A:
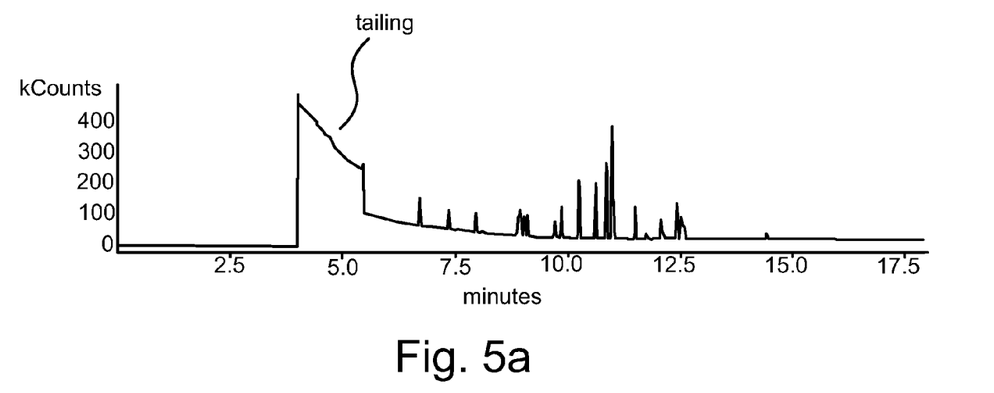
FIGS. 5a and 5b show a reproduction of chromatograms illustrating benefits of using a gas chromatography system with a check valve.
Figure 5B:
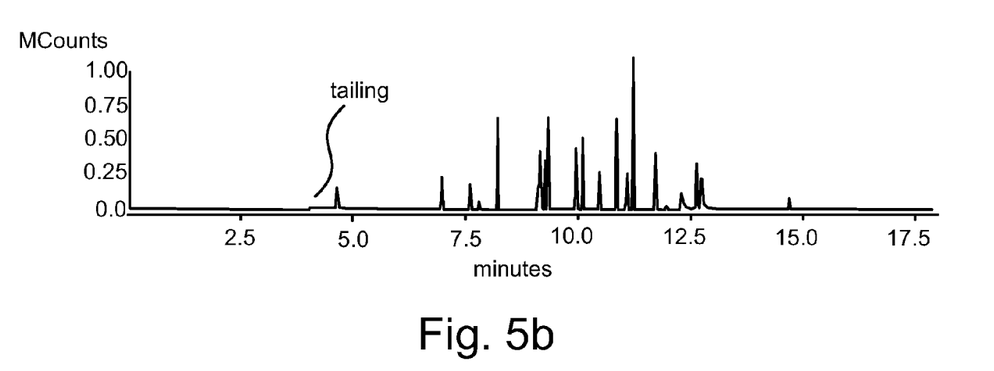

FIGS. 5a and 5b show chromatograms taken using a host fast injection into a gas chromatography system 100. FIG. 5a shows the chromatogram when the hot fast injection is made without a check valve 112 in the gas chromatographer. FIG. 5b shows the chromatogram when it is made using a GC system 100 with a check valve 112 under comparable conditions to those used to generate the chromatogram shown in FIG. 5a.

Of note is the reduction of the tailing between FIGS. 5a and 5b. Solvent tailing dominates the chromatogram shown in FIG. 5a. In contrast, the tailing in the chromatogram shown in FIG. 5b is significantly reduced. In addition, the recovery of the constituents of the injection and the signal intensity in FIG. 5b is superior to that in FIG. 5a. As shown in FIGS. 5a and 5b, situating a check valve 112 between the injector 114 and the electronic flow control module 110 markedly improves the quality of the chromatograms, particular in situations where high sensitivity is required.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A gas chromatography system comprising:
an electronic flow control module for providing a carrier gas;
an injector for receiving a liquid sample;
a vaporizer for vaporizing the liquid sample introduced into the injector;
a gas delivery line connecting the electronic flow control module and the injector, the gas delivery line allowing flow of carrier gas from the electronic flow control module to the injector;
a column connected to the injector, the column comprising a stationary phase, wherein the carrier gas elutes the vaporized sample through the column;
a check valve situated in the gas delivery line downstream of the electronic flow control module and upstream of the injector, the check valve sealing in response to a change in pressure in the injector that reverses flow in the gas chromatography system and substantially preventing back flow of liquid sample and vaporized sample into the gas delivery line; and
a detector providing a response signal representing output of the column.

2. The system of claim 1, wherein the gas chromatography system is a gas chromatography hyphenated system, the system further comprising a column outlet that is one of at vacuum or near vacuum.

3. The system of claim 1, wherein the injector is a split/splitless injector.

4. The system of claim 1, the check valve further comprising: a valve body comprising a channel; a seat located within the channel, the seat comprising an aperture; and a conical plug that engages the sides of the aperture and seals the aperture in response to the change in pressure in the injector that reverses flow in the gas chromatography system.

5. The system of claim 4, the check valve further comprising a gas delivery line outlet connecting the check valve to the injector through the gas delivery line, and a gas delivery line inlet connecting the check valve to the electronic flow control module through the gas delivery line.

6. The system of claim 5, the check valve further comprising a filter that filters contaminant that backs into the check valve through the gas delivery line outlet.

7. A gas chromatography system comprising:
an electronic flow control module providing a carrier gas that elutes a sample through a column;
an injector for receiving a sample;
a vaporizer for vaporizing the sample introduced into the injector;
a gas delivery line connecting the electronic flow control module and the injector, the gas delivery line facilitating flow of carrier gas from the electronic flow control module to the injector;
a column comprising a stationary phase, the column connected to the injector, the carrier gas and vaporized sample passing through the column; and
a check valve situated in the gas delivery line downstream of the electronic flow control module and upstream of the injector, the check valve comprising:
a valve body;
a first connection connecting the check valve to the injector;
a second connection connecting the check valve to the electronic flow control module;
a seat situated between the first connection and the second connection, the seat comprising an aperture; and
a conical plug situated in the aperture and sealing the aperture when the conical plug is depressed, the apex of the conical plug directed towards the second connection.

8. The system of claim 7, wherein the gas chromatography system is a gas chromatography-mass spectrometry system and further comprises a mass spectrometer that provides a signal representing output of the column.

9. The system of claim 7, wherein the conical plug is depressed in response to over-pressurization in the injector during sample volatilization, the check valve substantially preventing back flow of sample into the gas delivery line.

10. The system of claim 7, wherein the aperture has angled walls and the conical plug has an exterior angle equal to the angle of the angled walls.

11. The system of claim 7, the check valve further comprising a filter that filters contaminant flowing from the injector into the check valve through the gas delivery line.

12. The system of claim 7, the check valve further comprising a lip located at the base of the conical plug that engages the top of the seat when the conical plug is depressed.

* * * * *